US012586453B2

(12) United States Patent
White et al.

(10) Patent No.: US 12,586,453 B2
(45) Date of Patent: Mar. 24, 2026

(54) SYSTEM AND METHOD FOR MONITORING LIFE SIGNS OF A PERSON

(71) Applicant: Innovative Health Monitoring LLC, Stamford, CT (US)

(72) Inventors: Eric Gregory White, Tinton Falls, NJ (US); David Robert Abrams, Woodbridge, NJ (US); Federico Guerrero-Reyes, Woodbridge, NJ (US)

(73) Assignee: Innovative Health Monitoring LLC, Stamford, CT (US)

( * ) Notice: Subject to any disclaimer, the term of this patent is extended or adjusted under 35 U.S.C. 154(b) by 0 days.

(21) Appl. No.: 18/519,407

(22) Filed: Nov. 27, 2023

(65) Prior Publication Data

US 2024/0203227 A1    Jun. 20, 2024

Related U.S. Application Data

(63) Continuation of application No. 16/239,501, filed on Jan. 3, 2019, now abandoned, which is a
(Continued)

(51) Int. Cl.
| | |
|---|---|
| *G08B 21/02* | (2006.01) |
| *A61B 5/00* | (2006.01) |
| *A61B 5/113* | (2006.01) |
| *G01S 7/00* | (2006.01) |
| *G01S 7/292* | (2006.01) |
(Continued)

(52) U.S. Cl.
CPC ........ *G08B 21/0208* (2013.01); *A61B 5/0002* (2013.01); *A61B 5/113* (2013.01); *G01S 7/003* (2013.01); *G01S 7/2923* (2013.01); *G01S*

*7/415* (2013.01); *G01S 13/867* (2013.01); *G01S 13/88* (2013.01); *G06V 20/36* (2022.01); *G06V 20/52* (2022.01); *G06V 40/20* (2022.01); *G08B 21/0415* (2013.01); *G08B 21/0492* (2013.01);
(Continued)

(58) Field of Classification Search
CPC ............................... A61B 7/003; A61B 5/113
See application file for complete search history.

(56) References Cited

U.S. PATENT DOCUMENTS

| | | | |
|---|---|---|---|
| 7,403,638 | B2 | 7/2008 | Jeung et al. |
| 7,417,727 | B2 | 8/2008 | Polonskiy et al. |
(Continued)

FOREIGN PATENT DOCUMENTS

| | | |
|---|---|---|
| CN | 102835958 A | 12/2012 |
| CN | 103110422 B | 5/2013 |
(Continued)

*Primary Examiner* — Mainul Hasan
*Assistant Examiner* — Christopher Kingsbury Glover
(74) *Attorney, Agent, or Firm* — Greenberg Traurig, LLP

(57) ABSTRACT

A system and method for monitoring a person within a defined area by detecting breathing, or the lack thereof. Breathing is detected using radar signals, camera signals and/or microphone signals. The radar signals, camera signals and/or microphone signals are analyzed to determine if the subject person is moving, and if not moving if the person is breathing or not-breathing. An alarm is generated should the reflected radar signals, the camera signals and the microphone signals all simultaneously indicate no movement and no movement of the subject person in the defined area for a selected period of time.

20 Claims, 9 Drawing Sheets

Related U.S. Application Data continuation-in-part of application No. 15/658,271, filed on Jul. 24, 2017, now abandoned.

(60) Provisional application No. 62/718,206, filed on Aug. 13, 2018, provisional application No. 62/614,164, filed on Jan. 5, 2018, provisional application No. 62/377,035, filed on Aug. 19, 2016.

(51) Int. Cl.

| | |
|---|---|
| *G01S 7/41* | (2006.01) |
| *G01S 13/86* | (2006.01) |
| *G01S 13/88* | (2006.01) |
| *G06V 20/00* | (2022.01) |
| *G06V 20/52* | (2022.01) |
| *G06V 40/20* | (2022.01) |
| *G08B 21/04* | (2006.01) |
| *H04N 7/18* | (2006.01) |

(52) U.S. Cl.

CPC ............ *H04N 7/188* (2013.01); *A61B 5/4818* (2013.01); *A61B 2503/04* (2013.01); *H04N 7/185* (2013.01)

(56) References Cited

U.S. PATENT DOCUMENTS

| | | | |
|---|---|---|---|
| 7,502,643 | B2 | 3/2009 | Farringdon et al. |
| 9,311,715 | B2 | 4/2016 | Rafii et al. |
| 10,327,073 | B1 | 6/2019 | McElhone et al. |
| 2002/0173696 | A1* | 11/2002 | Kolarovic ............... A61B 5/01 600/549 |
| 2003/0201894 | A1 | 10/2003 | Li |
| 2008/0294019 | A1* | 11/2008 | Tran ...................... G16H 15/00 600/301 |
| 2012/0022348 | A1 | 1/2012 | Droitcour et al. |
| 2014/0142729 | A1 | 5/2014 | Lobb et al. |
| 2014/0297217 | A1 | 10/2014 | Yuen |
| 2015/0141762 | A1* | 5/2015 | Heinrich ............. A61B 5/1128 600/301 |
| 2016/0094812 | A1 | 3/2016 | Chen |
| 2016/0135734 | A1 | 5/2016 | Schindhelm |
| 2016/0313442 | A1* | 10/2016 | Ho ....................... G01S 13/867 |
| 2016/0367202 | A1 | 12/2016 | Carter et al. |
| 2017/0055877 | A1* | 3/2017 | Niemeyer ........... A61B 5/0077 |
| 2017/0359506 | A1* | 12/2017 | Manzari ................ H04N 23/65 |
| 2018/0035082 | A1* | 2/2018 | Patil ........................ A61B 5/45 |
| 2019/0159674 | A1 | 5/2019 | Kogure |
| 2020/0105400 | A1 | 4/2020 | Alvelda et al. |
| 2020/0359913 | A1 | 11/2020 | Ghodrati et al. |

FOREIGN PATENT DOCUMENTS

| | | |
|---|---|---|
| CN | 104133199 A | 11/2014 |
| JP | 2004537335 A | 12/2004 |
| WO | 2002062282 A1 | 8/2002 |

* cited by examiner

SYSTEM AND METHOD FOR MONITORING LIFE SIGNS OF A PERSON

RELATED APPLICATIONS

This application is a continuation of U.S. patent application Ser. No. 16/239,501, filed Jan. 3, 2019, which claims benefit and priority to Provisional Patent Application No. 62/614,164 filed Jan. 5, 2018, and claims benefit and priority to Provisional Patent Application No. 62/718,206 filed Aug. 13, 2018, and is a continuation-in-part of U.S. patent application Ser. No. 15/658,271, filed Jul. 24, 2017, which claims the benefit of Provisional Patent Application No. 62/377, 035, filed Aug. 19, 2016.

BACKGROUND OF THE INVENTION

1. Field of the Invention

In general, the present invention relates to monitoring equipment that can monitor the life signs of a person as that person sleeps. More particularly, the present invention relates to monitoring equipment that monitors life signs using low-energy radar, cameras, and/or microphones.

2. Prior Art Description

There are many monitoring systems that are designed to monitor various life signs. For example, in an intensive care unit of a hospital, patients are attached to heart rate monitors, blood pressure monitors, blood oxygen monitors and the like. Should any of these monitors detect a condition outside an acceptable threshold, an alarm is sounded.

In a hospital setting, the various sensors are typically wired sensors that are attached directly to the body. This makes the sensors very accurate and resistant to interfering signal noise from outside sources.

Monitoring devices are also used in a variety of ways outside of a hospital. For instance, parents often use baby monitors to monitor their children when they sleep. Such monitoring typically occurs from the time the child is an infant until the child is old enough to not need a crib. The monitoring is performed for many reasons. Infants are susceptible to Sudden Infant Death Syndrome (SIDS). As infants grow and begin to move, they also face dangers from accidental strangulation and choking. Once the child is old enough to stand and climb, the child faces dangers from falling and entrapment. Monitoring is also used on adults, such as those who have sleep apnea or those who have a high risk of mortality due to disease or age.

When monitoring is used on a child or a mobile adult, wired sensors are rarely used. The wires of sensors create strangulation hazards and tripping hazards. As such, the potential harm can outweigh the potential good. Accordingly, most monitoring equipment sold for in-home use relies on wireless monitoring. The most common wireless monitoring system is a camera and microphone system, commonly referred to as a baby monitor. These devices are placed in the room and are directed toward a crib or bed. The baby monitor transmits images of the crib or bed, along with any detected audio signals to a remote receiver. A person viewing the display of the receiver can view any movement in the crib or bed and can hear if the occupant of the crib or bed is crying or making any sounds of distress.

The disadvantages of a traditional baby monitor system are obvious. The baby monitor only detects movement and sound. If an infant has a SIDS event, there may be no movement or sound. Likewise, if an adult passes away while sleeping, there may be no movement or sound.

Recognizing the disadvantages, improved monitoring devices have been developed for in-home use. Some of these monitoring devices use low energy radar to monitor a sleeping person. The radar is sensitive enough to detect the slow expansion and contraction of the chest as a person inhales and exhales. Such prior art monitoring systems are exemplified by Chinese Patent Disclosure No. CN104133199A and Chinese Patent Disclosure No. CN103110422A.

Radar-based monitoring systems also have some disadvantages. Even if a directional antenna is used, radar energy propagates from the antenna in all directions. This creates an omni-directional area of coverage. As a consequence, the radar system can detect movement from objects, pets, and people well away from the crib or bed being monitored. Movement from non-targets objects, pets and people can be wrongly interpreted as movement within the crib or bed by the monitoring system. Accordingly, if a person stops breathing, the falsely detected movements can delay or prevent the danger from being detected.

In the prior art, monitoring systems have been developed that are hybrids of traditional camera baby monitors and low-energy radar monitors. Such prior art systems monitor a person in a crib or bed with both a camera and a radar transceiver. However, the outputs of the camera system and the radar system are not cross-correlated. Rather, if the radar system detects an alarm condition, the camera system is merely there to see if the alarm is a false alarm. If the person being monitored stops breathing and the radar fails to detect the condition due to false returns, the camera system will not detect the danger. Such prior art hybrid systems are exemplified by U.S. Patent Application Publication No. 2016/0313442 to Ho, and Chinese Patent Disclosure No. CN102835958.

The signals captured by a radar system and/or a camera system that contain relevant data can easily be washed out by noise and signals that contain irrelevant data. For instance, the chest movement of a sleeping infant wrapped in a tight blanket are very small. Detecting such movements using low energy radar and/or a camera is difficult. The movements caused by breathing are buried in signals caused by body movements, signals caused by movements in the surrounding environment, and signal noise. Accordingly, signal processing algorithms must be used to separate the useful signals from the noise and the irrelevant signals. The signal processing algorithms used in the prior art tend to produce a high number of false alarms in the hope of never missing a real alarm. However, the large number of false alarms make prior art systems unpopular and cause people to stop using the systems after experiencing a string of false alarms. Thus, many prior art monitoring systems are no better than having no monitoring system at all.

A need therefore exists for a wireless monitoring system that can monitor a person in a crib or bed by detecting even the smallest movement caused by breathing. A need also exists for such a system that can separate useful signals from noise and irrelevant signals to produce a more reliable system with less false alarms. A need also exists for such a system that can analyze signals in real time without having to perform signal analysis at a remote location. These needs are met by the present invention as described and claimed below.

SUMMARY OF THE INVENTION

The present invention is a system and method for wirelessly monitoring a person. The system can detect breathing, or the lack thereof, in a subject person, such as an infant in a crib or an adult with sleep apnea.

The system and method can detect breathing using radar signals, camera signals and/or microphone signals. Using a radar transceiver, radar signals are directed toward an area in which the subject person is sleeping. The radar signals reflect from the subject person, therein creating reflected radar signals. Contained within the reflected radar signals is data that references the rhythmic movements of breathing and/or the beating heart.

Likewise, a camera is directed toward the area in which the subject person is sleeping. The camera detects movements of the subject person. Contained within the detected movements are movements caused by rhythmic breathing and/or the beating heart.

At least one microphone also monitors the area of the subject person. The microphone detects sounds made by the subject person. Contained within the detected sounds are the sounds caused by rhythmic breathing.

The reflected radar signals, the signals from the camera, and the signals from the microphone are fused to determine if the subject person is moving, and if not moving if the person is breathing or not-breathing. An alarm is generated should the reflected radar signals, the camera signals and the sound signals all simultaneously indicate no movement and no breathing of the subject person.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention monitoring system can be used in many institutional settings, such as hospitals and nursing homes, the system is particularly well suited for in-home use. Accordingly, an exemplary embodiment of the monitoring system is selected for the purposes of description and illustration that shows the present invention being used in a home to monitor a person in a bed or crib. The illustrated embodiment, however, is merely exemplary and should not be considered a limitation when interpreting the scope of the appended claims.

Figure 1:
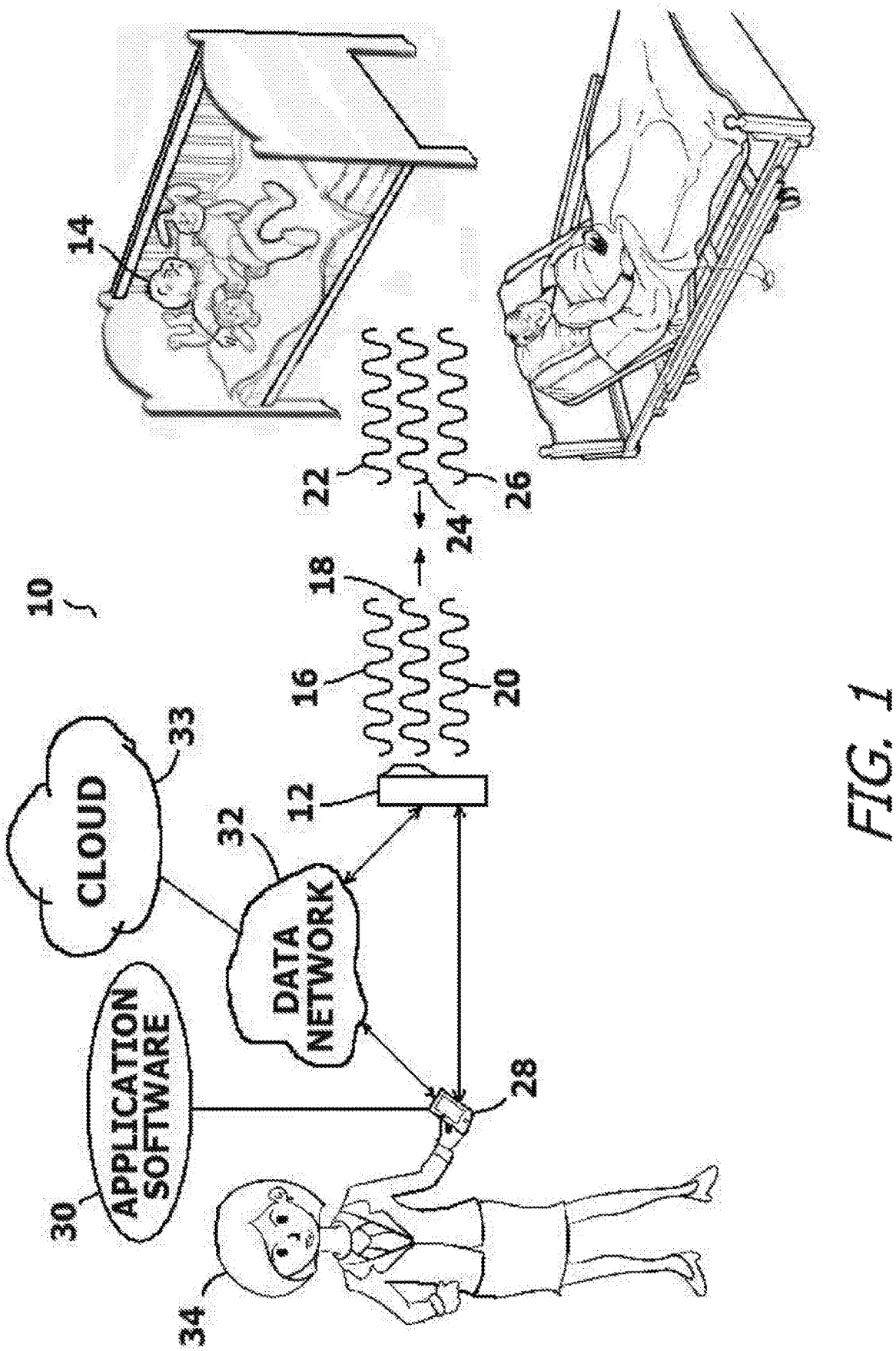
FIG. 1 shows an exemplary embodiment of the present invention monitoring system.

Referring to FIG. 1, an overview of the monitoring system 10 is shown. The monitoring system 10 includes a monitoring unit 12. The monitoring unit 12 is placed in a room and is directed toward a subject person 14, such as a child in a crib or an adult in bed. In the preferred embodiment, the monitoring unit 12 can actively emit light 16, radar signals 18 and audio signals 20. The light 16 emitted are preferably in the infrared spectrum so as not to be visible to the subject person 14. The emitted radar signals 18 are low-energy signals that are harmless to the subject person 14 and any other sensitive electronic equipment, such as a pacemaker. The emitted audio signals 20 are audible to the subject person 14 being monitored. As will later be explained, the audio signals 20 can be music, an alarm or the transmitted voice of another person.

The monitoring unit 12 receives light 22, reflected radar signals 24 and ambient sounds 26. The light 22 received includes existing ambient light and light returned from any illumination projected by the monitoring unit 10. The reflected radar signals 24 are the returns from the radar emitted by the monitoring unit 10. The ambient sounds 26 are any audible sounds detected by the monitoring unit 10. The light 22, reflected radar signals 24 and ambient sounds 26 received by the monitoring unit 10 are all internally processed. The monitoring unit 10 uses circuitry and processing software to specifically extract features that are associated with the breathing of the subject person 14. The monitoring unit 10 processes the light 22, reflected radar signals 24, and ambient sounds 26 in real time. The processed information can be accessed by a remote computing device 28, such as a smart phone, running the application software 30 needed to display the processed signal information. Depending upon the location of the remote computing device 28, the processed signals can be shared directly with the remote computing device 28 or can be forwarded to the remote computing device 28 through a data network 32, such as a cellular network or the Internet.

An observer 34, such as a parent or nurse, can view the remote computing device 28 and receive the processed information. As will later be explained, the processed information is formatted in a user-friendly manner. Likewise, if an alarm condition is detected by the monitoring unit 12, the observer 34 is instantly informed. The observer 34 can communicate with the monitoring unit 12 and causing the monitoring unit 12 to broadcast music or words that can be heard by the subject person 14 being monitored. In such a manner, a subject person 14 who is agitated can be pacified and a subject person 14 in distress can be comforted until help arrives on scene.

Figure 2:
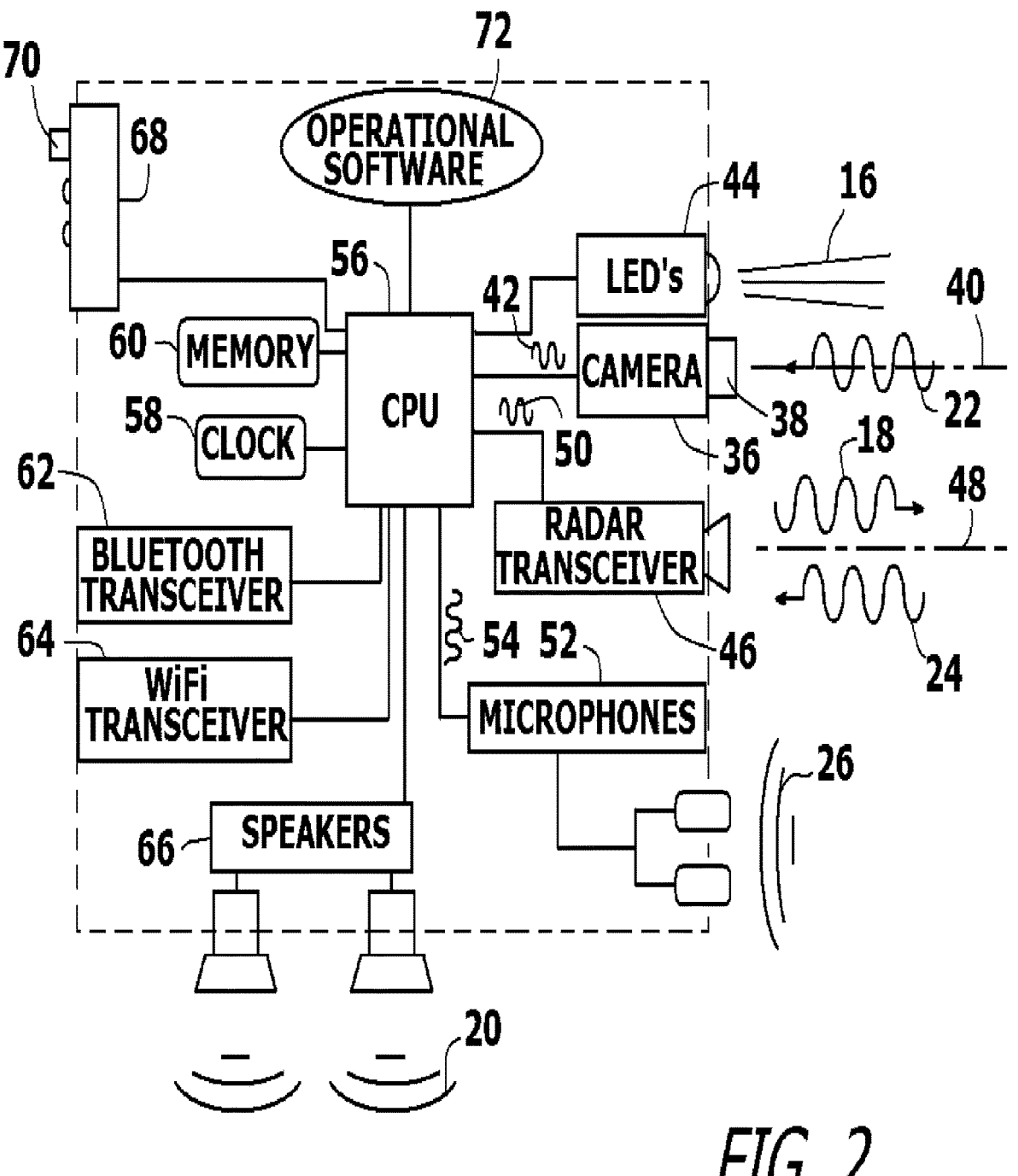
FIG. 2 shows a schematic of the monitoring unit used by the present invention monitoring system.

Referring to FIG. 2, the primary components of the monitoring unit 12 are shown and explained. The monitoring unit 12 contains a camera 36 for imaging the sleeping area in a crib, bed, bassinet or the like. The camera 36 preferably has the ability to image the visible light spectrum and at least some of the infrared spectrum. In this manner, the camera 36 can image in daylight and in the dark.

The camera 36 has an objective lens 38. The objective lens 38 is directed in a particular direction that is shown by line 40. The objective lens 38 of the camera 36 is directed toward the subject person 14 being monitored. The light 22 captured by the camera 36 is converted into camera data 42 that is processed in a manner later described.

One or more LEDs 44 may be provided for illuminating the subject person 14 being monitored. The LEDs 44 are preferably IR LEDs that produce light that can be detected by the camera 36 but not by the eyes of the subject person 14 being monitored. It will be understood that the LEDs 44 are an economical source of IR light. However, other sources of IR light, such as low powered IR lasers or filtered polychromatic lights could also be used in the design. Regardless of the source of the IR light, the intensity of the light is sufficient to illuminate the area of the subject person 14 being monitored, therein enabling the camera 36 to image that area.

A radar transceiver 46 is provided. Although different radars can be used, the radar transceiver 46 preferably is a low powered pulse Doppler radar. In this manner radar transceiver 46 can detect both velocity and range. The radar transceiver 46 is configured to have its greatest range in a particular direction 48. The direction 48 of greatest range is parallel to the directional line 40 of the camera 36. As such, the radar transceiver 46 covers the same area as is being imaged by the camera 36. This causes the radar transceiver 46 to be more sensitive in the direction of the subject area. The radar transceiver 46 emits radar signals 18 covering the subject area and detects reflected radar signals 24 that return. The reflected radar signals 24 are detected by the radar transceiver 46 and are converted into radar data 50. The radar data 50 is processed in a manner that is later described.

One or more microphones 52 are provided as part of the monitoring unit 12. Preferably, at least two microphones 52 are used. The microphones 52 are oriented toward the subject area targeted by the camera 36 and radar transceiver 46. In this manner, any ambient sounds 26 originating within the subject area will be detected by the microphones 52. The microphones 52 produce audio data 54. The audio data 54 is processed in a manner that is later described.

A computing device 56 receives the camera data 42, the radar data 50 and the audio data 54. The computing device 56 contains a clock 58 that enables the data to be indexed by time. The computing device 56 can have a high capacity memory 60 or access to cloud memory 33 through the data network 32 so that large caches of time indexed data to be stored for later review.

The computing device 56 can exchange data with outside sources using a Bluetooth® transceiver 62 and/or a WiFi transceiver 64. Other data transmission systems can also be used, such as a cellular network transmission and/or a hardwire connection. The computing device 56 also controls one or more speakers 66. The speakers 66 can broadcast audio signals 20 into the environment of the monitoring unit 12. As will later be explained, the broadcast audio signals 20 can be soothing music that can lull a child to sleep or a piercing alarm that can bring help.

The computing device 56 is also connected to a user interface 68. The user interface 68 contains an on/off switch 70 for the monitoring unit 12 and may contain status lights and sensitivity controls that can be manually adjusted by a user.

The computing device 56 is programmable and runs specialized operational software 72. The operational software 72 is capable of being periodically updated with programming updates received through the Bluetooth® transceiver 62, the WiFi transceiver 64, or other data transmission system.

Figure 3:
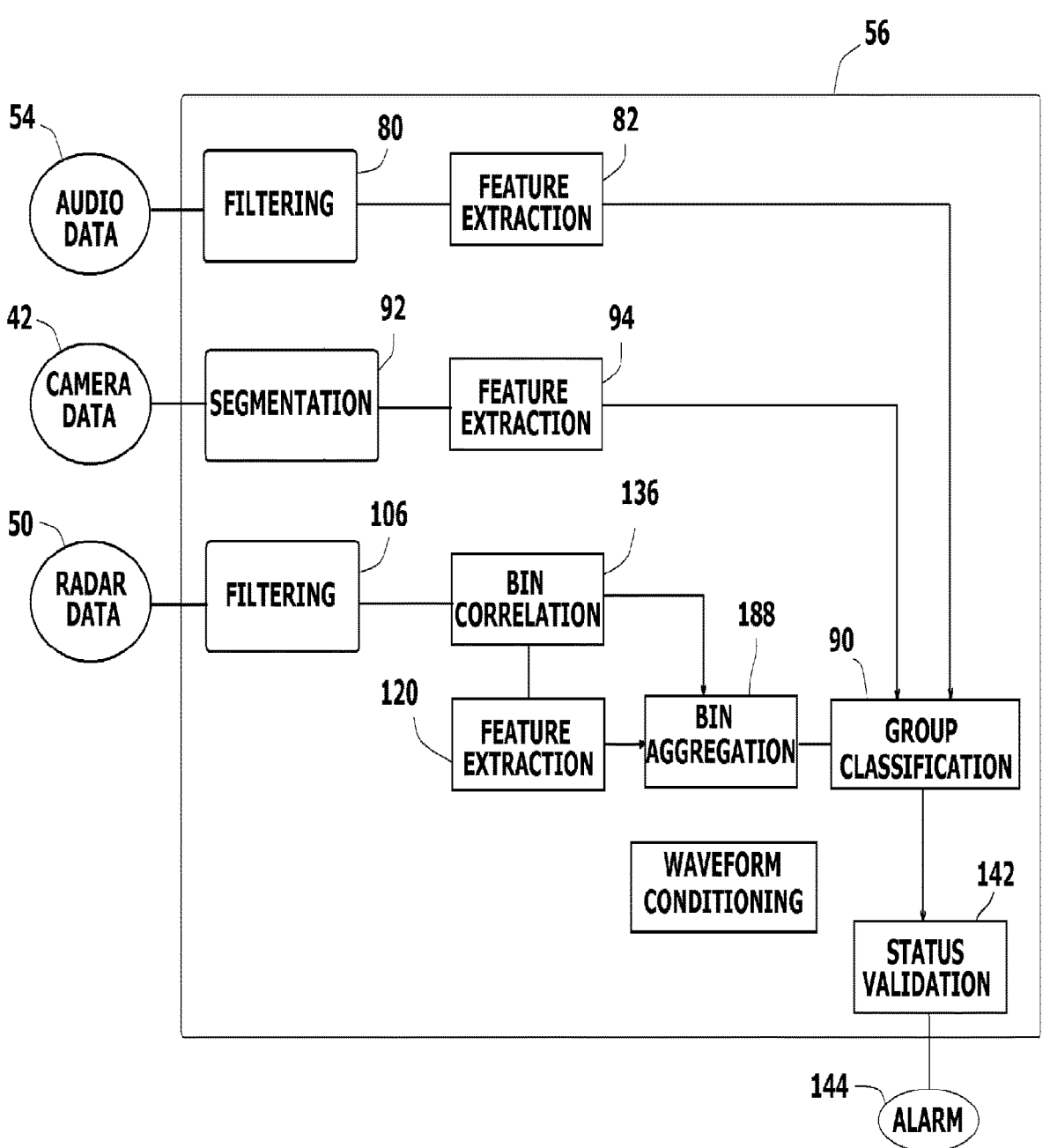
FIG. 3 shows a logic diagram that illustrates the operations performed within the monitoring unit.

Referring to FIG. 3 in conjunction with FIG. 2, it will be understood that the computer system 56 receives the audio data 54 from the microphones 52, the camera data 42 from the camera 36, and the radar data 50 from the radar transceiver 46. This data is analyzed by the computing system 56 using the operational software 72. The purpose of the analysis is to first determine if the subject person 14 is within the area being monitored. If the subject person 14 is in the monitored area, it will then extract features from within the audio data 54, the camera data 42 and the radar data 50 and determine if they are attributable to the breathing of the subject person 14. These features are then monitored for change. If the features indicate that the subject person 14 has stopped breathing, then an alarm is generated.

Referring to FIG. 3 in conjunction with FIG. 2, it can be seen that the computing system 56 processes the audio data 54, camera data 42 and radar data 50. All three sets of data are analyzed to detect signal features that are indicative of breathing.

The processing of the audio data 54 from the microphones 52 is first described. Both the sounds of crying and the sounds of breathing can be detected in the audio data 54. Detecting the sounds of crying can be accomplished using known sound processing techniques, such as those described in U.S. Pat. No. 9,020,622 to Shoham. What is far more intricate is effectively isolating the features in the sound audio data 54 that corresponds to the delicate sounds of breathing. To isolate the sounds of breathing, the audio data 54 from the microphones 52 is initially filtered. See Block 80. The filtering may include directional filtering, this may eliminate some sound signals that do not originate in the subject area. The directional filtering is optional. In a required filtering step, the ambient sound signals 26 are filtered in an attempt to isolate the sounds of breathing from other environmental noises. The required filtering includes subjecting the audio data 54 to a low pass filter 81. This attenuates signals with frequencies that are too high to represent breathing. After the audio data 54 is initially filtered, it is further processed to extract desired features, which in this case, are the sounds of breathing. See Block 82.

Figure 4:
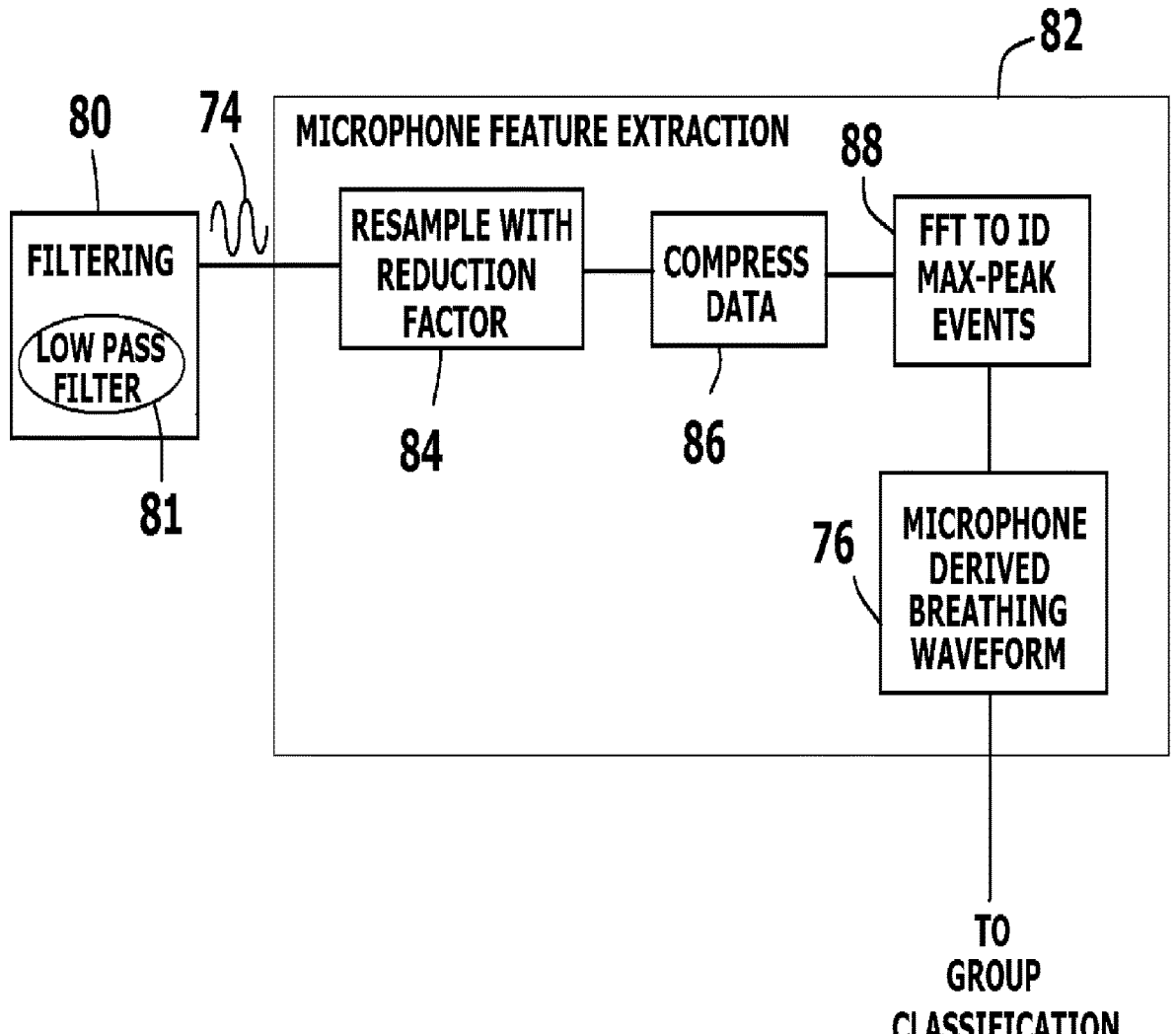
FIG. 4 is a block diagram that shows operational details of the microphone feature extraction process referenced in FIG. 3.

The details of the feature extraction process are shown in FIG. 4. Referring to FIG. 4 in conjunction with FIG. 3 and FIG. 2, it can be seen that a filtered audio signal 74 is obtained after the raw audio data 54 is filtered in the filtering process of Block 80. The goal of the feature extraction process is to extract a breathing waveform from the filtered audio signal 74. To extract a breathing waveform from the filtered audio signal 74, the filtered audio signal 74 is resampled with a reduction factor. See Block 84. A preferred reduction factor for the resampling is $\frac{1}{1000}$, however other reduction factors can be used. The resampled audio data is the compressed using an arctan function. See Block 86. The compressed audio data is then subjected to a fast Fourier transform to find the occurrences of max-peak signal events. See Block 88. These max-peak events correspond to the breathing waveform of interest. The resulting breathing frequency waveform 76 is later used in a group classification process. See Block 90

Figure 5:
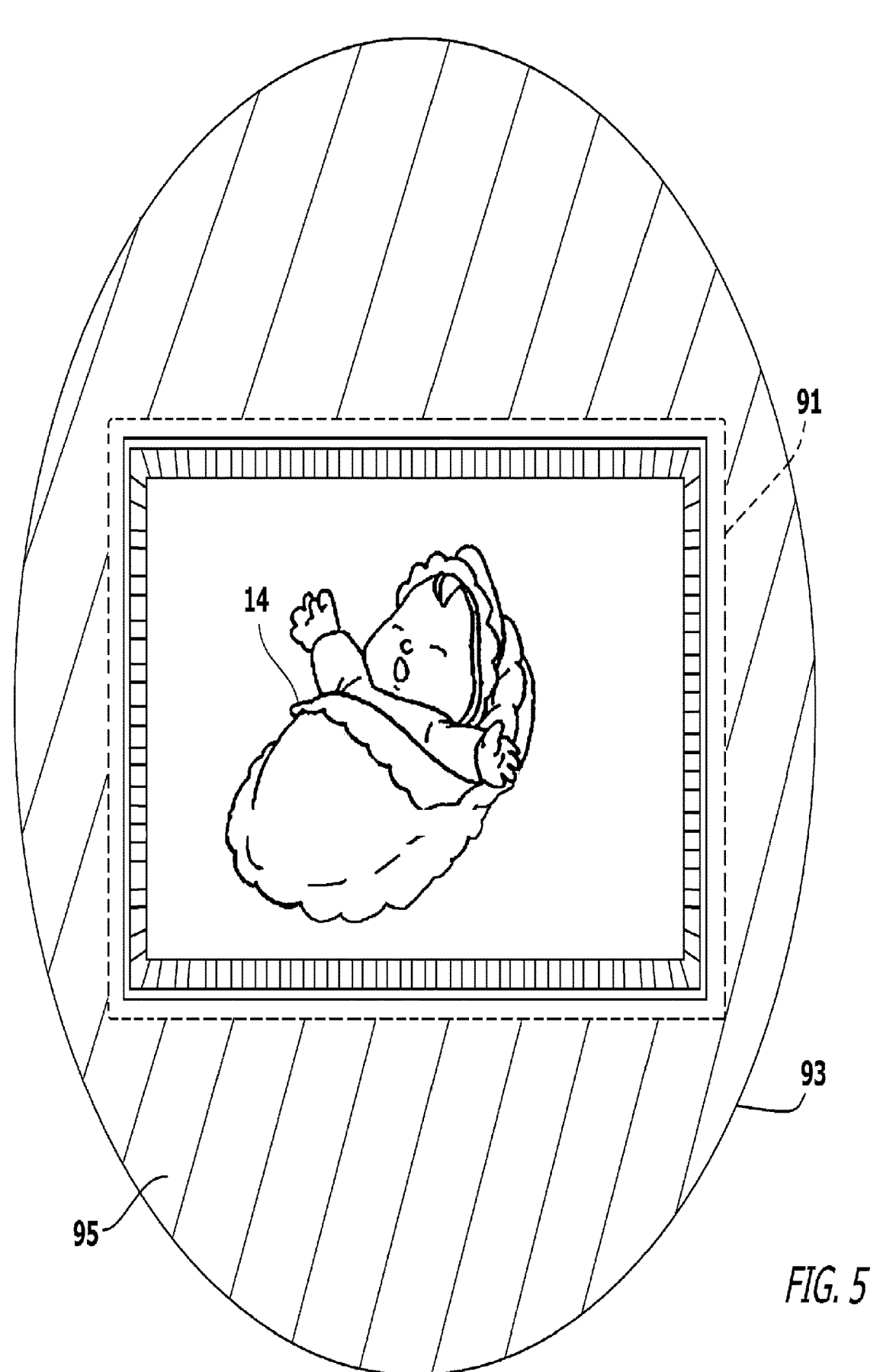
FIG. 5 shows a screen and indicates regions that can be segmented by a user.

Returning to FIG. 3 and FIG. 2, it is shown that the camera data 42 is also processed by the computing system 56. The camera data 42 is initially subjected to area segmentation. See Block 92. Upon the setup of the monitoring unit 12, the person setting the monitoring unit 12 in place, directs the camera 36 toward a crib or bed in the subject area. Referring to FIG. 5 with FIG. 3, it can be seen that the camera 36 has a field of view 93 that is imaged. A person looking at the image of the camera 36, can also manage the image within the field of view 93. The subject area 91 is selected as the area into which the subject person 14 is most likely located. The subject area 91 is typically the area of the crib mattress or bed mattress. The area surrounding the subject area 91 is then defined as the visitor area 95. This segmentation process is used to distinguish between movements that may be attributable to the subject person 14 from all other detected movements. Accordingly, when looking for the movements caused by breathing, the computer system 56 will only consider data that originates from within the selected subject area 91.

Figure 6:
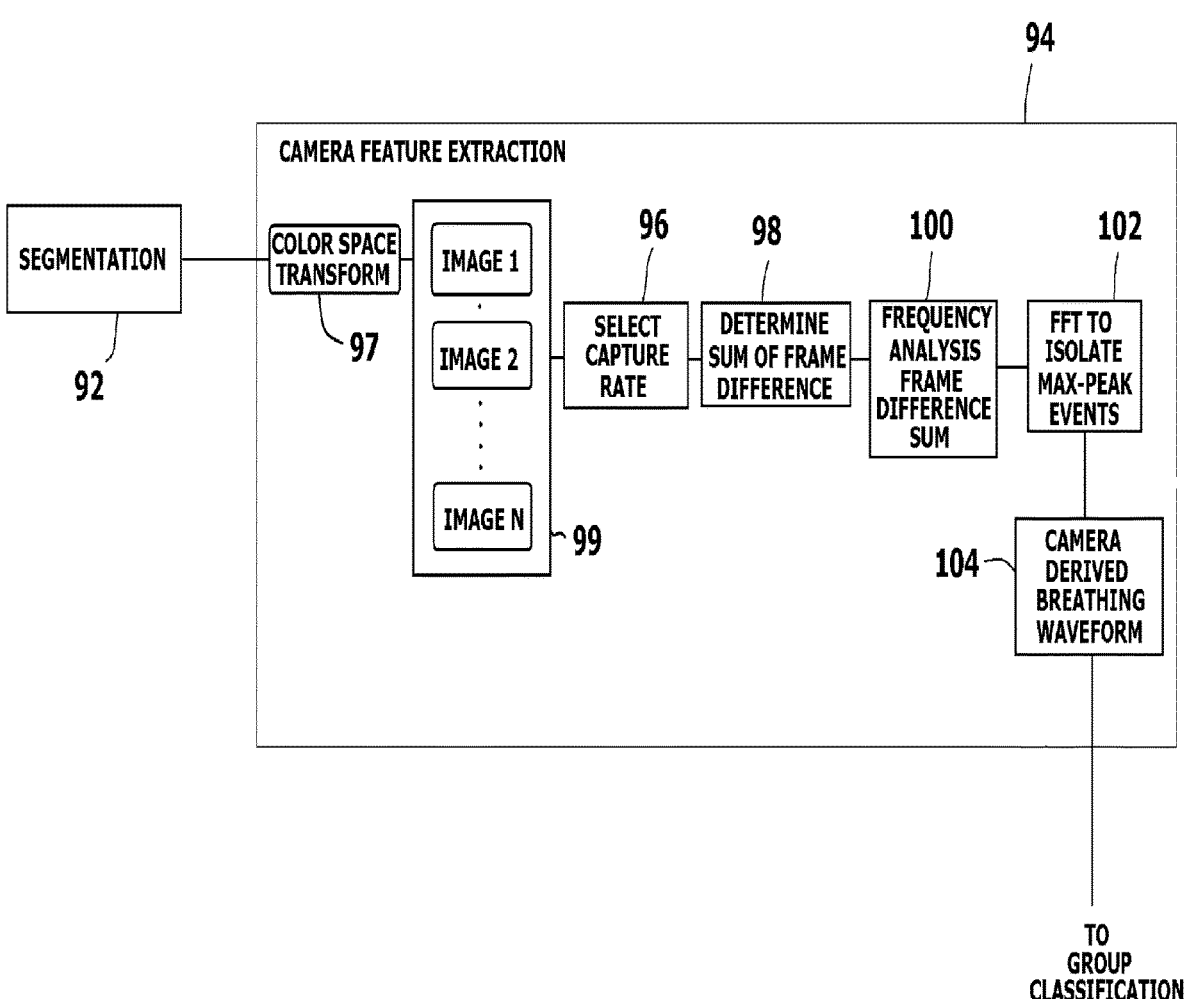
FIG. 6 is a block diagram that shows operational details of the camera feature extraction process referenced in FIG. 3.

Referring to FIG. 6 in conjunction with FIG. 2 and FIG. 3, it can be seen that after segmentation (Block 92), the camera data 42 is further processed to extract desired features, which in this case, are the movements associated with breathing. See Block 94. After field segmentation, the camera data 42 contains various frame images. The frames undergo a color space transform that changes the images from color to grayscale. See Block 97. This reduces the amount of processing needed to analyze the images, therein increasing response time for the system. The grayscale image frames are then stored in a circular buffer 99. The grayscale image frames are analyzed by the computing system 56 to determine movement. It will be understood that in order to analyze movement, images frames from different time points are compared. The image capture rate is dependent on framerate of the camera 36. Many cameras that are compatible with the system have a framerate that would require a capture rate of one frame per every ten to twenty-five frames. See Block 96

As is indicated by Block 98, subsequent captured frames are compared where the difference between image frames is the sum of the first frame minus the subsequent frame at the delay. Any differences in the image frame are indicative of movement that has occurred during the time of the delayed capture rate. The sum of the difference over time (buffer length=N) is subjected to frequency analysis to determine frequency of respiration as a feature. See Block 100.

By comparing image frames over time, rhythmic patterns of movement are detected. A fast Fourier transform is used to identify the max-peak signal events can be isolated that represent rhythmic movements. See Block 102. These rhythmic patterns of movement are distinguishable over random periods of body movement. The rhythmic patterns correlate to movements caused by breathing and/or the beating heart. The result is a camera derived breathing waveform of heartbeat waveform that is later used in a group classification process. See Block 104.

Figure 7:
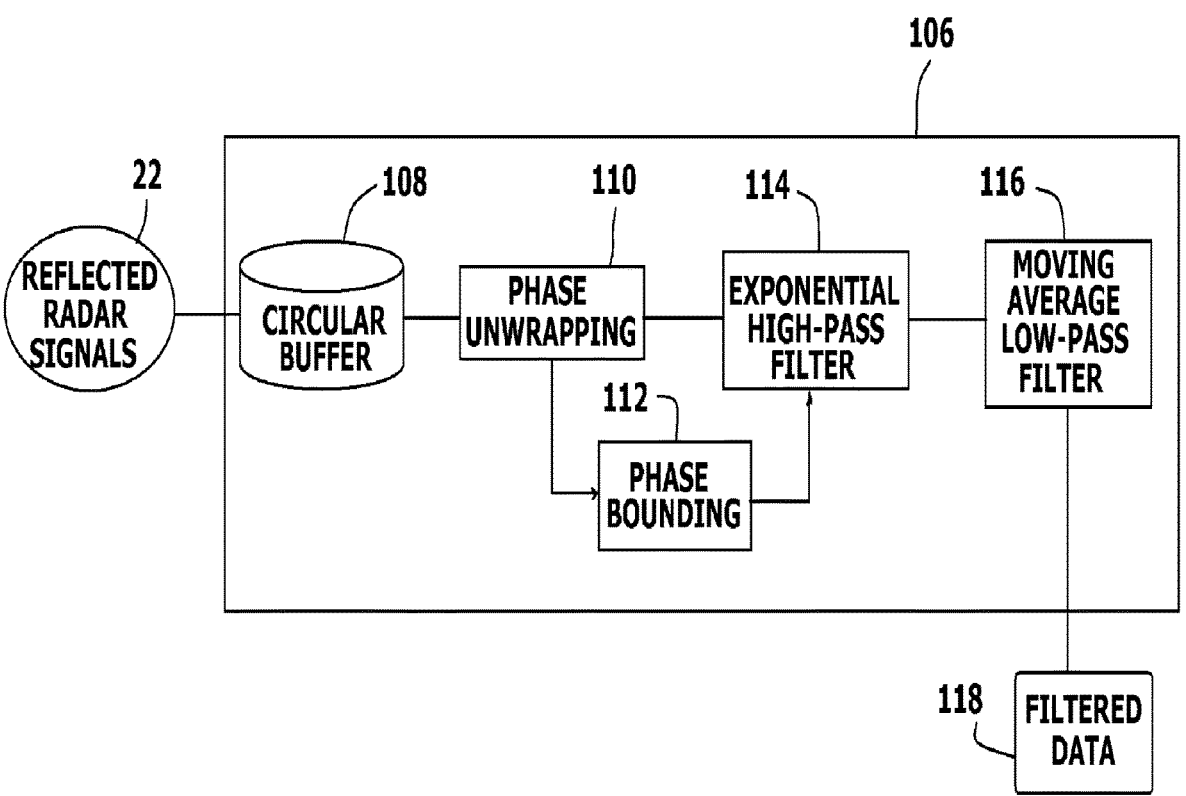
FIG. 7 is a block diagram that shows operational details of the radar signal filtering process referenced in FIG. 3.

The computing system 56 also analyzes the reflected radar signals 24 in an attempt to detect movements associated with breathing and/or the beating heart. Referring to FIG. 7 in conjunction with FIG. 3 and FIG. 2, it will be understood that the reflected radar signals 24 are initially filtered, as indicated by Block 106. To filter the reflected radar signals 24, the signals fed into a circular buffer 108. The incoming reflected radar signals 24 are phase bounded and need to undergo phase unwrapping and phase bounding. See Block 110 and Block 112. The unwrapped signal are passed through an exponential high pass filter so that the waveform is zero centered. See Block 114. The unwrapped, high filtered data is then subjected to a moving average low pass filter to smooth the data. See Block 116. This creates the filtered data 118. The targeted features are extracted from the filtered data 118. The targeted features are the returns that correspond to movement caused by breathing and/or the beating heart. See Block 120 in FIG. 3.

Figure 8:
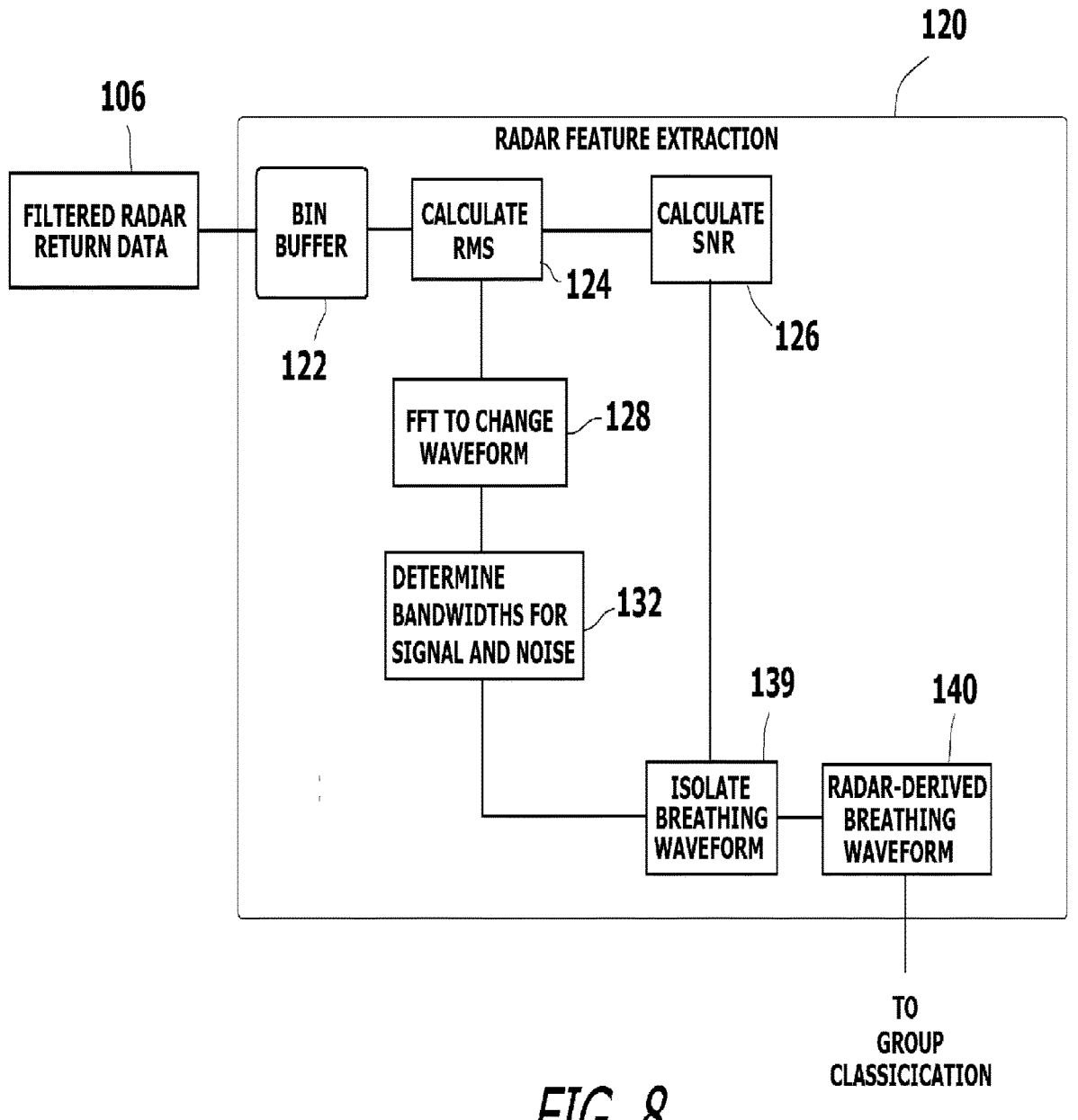
FIG. 8 is a block diagram that shows operational details of the radar feature extraction process referenced in FIG. 3.

Referring to FIG. 8 in conjunction with FIG. 3 and FIG. 2, it can be seen that the filtered radar return data 118 is arranged in bin buffers 122. Once a bin buffer 122 is full, the root mean square is calculated. See Block 124. With the root mean square of each bin buffer known, a signal-to-noise ratio is calculated. See Block 126. A true signal-to-noise ratio cannot be directly calculated without a-priori knowledge of the signal. As such, certain assumptions must be made to make the calculation possible. The breathing rate of the person being monitored is assumed to be between 15 breaths per minute and 60 breaths per minute. This translates to a breathing rate of between 0.25 Hz and 1 Hz. If the heartbeat is being detected a slightly higher rate is utilized. Using the root mean square data, a fast Fourier transform is implemented to change the waveform from a time domain to a frequency domain. See Block 128. This creates a transformed waveform 130. Additionally, a window is applied to each time frame of the bin buffer 122 to prevent wrapping boundary effects. Using the transformed waveform 130, the maximum spectral magnitude and its corresponding frequency can be calculated.

The transformed waveform 130 contains both useful signals and noise. These aspects must be separated. See Block 132. To distinguish signals from noise in the transformed waveform 130, the fundamental frequency of the subject's breathing rate is determined by calculating the maximum component of the fast Fourier transform in the assumed breathing rate frequency of 0.25 Hz to 1.0 Hz. From the maximum component, the waveform is walked left and right until it reaches thirty (30%) of its peak value. This bandwidth at this selected value is defined as the bandwidth of the signal. The remainder of the waveform is designated as noise. If the peak value is found to be near the waveform extremes, i.e. frequency equal to zero or equal to FT length/2, then the peak is considered invalid and a subsequent bin buffer is analyzed.

Likewise, if another high value is found within the fast Fourier transform range that is larger than the originally calculated peak value, then the peak value is considered invalid and another bin buffer is analyzed.

The data from the various buffer bin analyses is then correlated in a bin correlation step and then aggregated in a bin aggregation step. See Block 136 and Block 138 in FIG. 3. During bin correlation, the waveforms corresponding to each processed buffer bin is digitized into "1's" and "0's". This is accomplished by setting a threshold and assigning "1's" to values above the threshold and "0's" to values under the threshold. This creates groups. Subsequent groups are then compared using a ~XOR comparator. The results are saved to a correlation matrix. Changes in the field are quickly identified due to the simple comparison and corresponding rapid processing time. The area of correlated data identified in the radar field is used to identify the location of the monitored person in the radar field. Once the location of the person is identified, the analysis of the radar return data 50 can be limited to the returns from the identified area.

During bin aggregation, the bins identified as containing the data from the person being monitored are grouped. In each group, the range bin having the maximum signal-to-noise ratio is identified. In each group, each range bin is analyzed to sum the signal-to-noise ratio if the signal-to-noise ratio exceeds a percentage of the group's maximum signal-to-noise ratio. Subsequent groups are analyzed to determine how well they match the first group. The group with the highest match score is selected as the next group. At this point in the analysis, the data attributable to the person being monitored is isolated and the signal-to-noise ratio is known. Using these variables, the radar derived breathing waveform 140 can be isolated that most probably represents the rhythmic breathing of the person being monitored. See Block 139.

From the prior analysis, the microphone derived breathing waveform 76, the camera derived breathing waveform 104 and the radar derived breathing waveform 140 are known.

The waveforms 76, 104, 140 are then classified using a group classification process. See Block 90. The three classifications used in the present invention system are breathing, no-movement, and movement. All groups are defaulted to the no-movement state. If any waveform from any source indicates breathing, then the net result of the whole group is set to breathing. Likewise, if any waveform from any source indicates movement of the person being monitored, then the net result of the whole group is set to movement. However, if all sources indicate a state of no-movement for a selected period of time, an alarm condition occurs. The sensitivity of the system can be controlled by controlling waveform thresholds and applying probability functions to the data for each class.

As is indicated by Block 142, once a class of waveform is determined, it is validated. The validation is used to reduce the occurrences of false alarms. The default state is the state of no-movement, which is the alarm state. The existing state can only be changed if the new state persists for a selected period of time. The period of time is adjustable and is preferably between 1 and 10 seconds. As such, if the system detects breathing or movement for the set period of time, the default no-movement state is replaced with either the breathing state or the movement state. The no-movement state will not be reinstated until breathing or movement is not detected for the duration of the threshold time period. As is indicated by Block 144, if the no-movement state is recognized for the threshold time period, then an alarm is sent.

Returning to FIG. 1, it will be understood that when an alarm is sent, the alarm is first sent to the remote computing device 28 of the observer 34. The remote computing device 28 will provide the observer 34 with both an audio and visual alarm. Using the remote computing device 28, the observer 34 can live-stream the camera data 42 and the audio data 54. From this, the user may be able to quickly ascertain that the alarm is a false alarm. For instance, the observer 34 may be able to see that the subject person 14 being monitored simply woke up and left the monitored area of the crib or bed.

If the alarm condition does appear to be real, the observer 34 has certain options. First, the observer 34 can cause the monitoring unit 12 to sound a loud audible alarm. This may be able to startle a sleeping person into breathing. Additionally, the observer 34 can stream live audio to the monitoring unit 12. This will enable the observer 34 to speak to the person being monitored and hopefully can be used to rouse the person back to conscious breathing.

Figure 9:
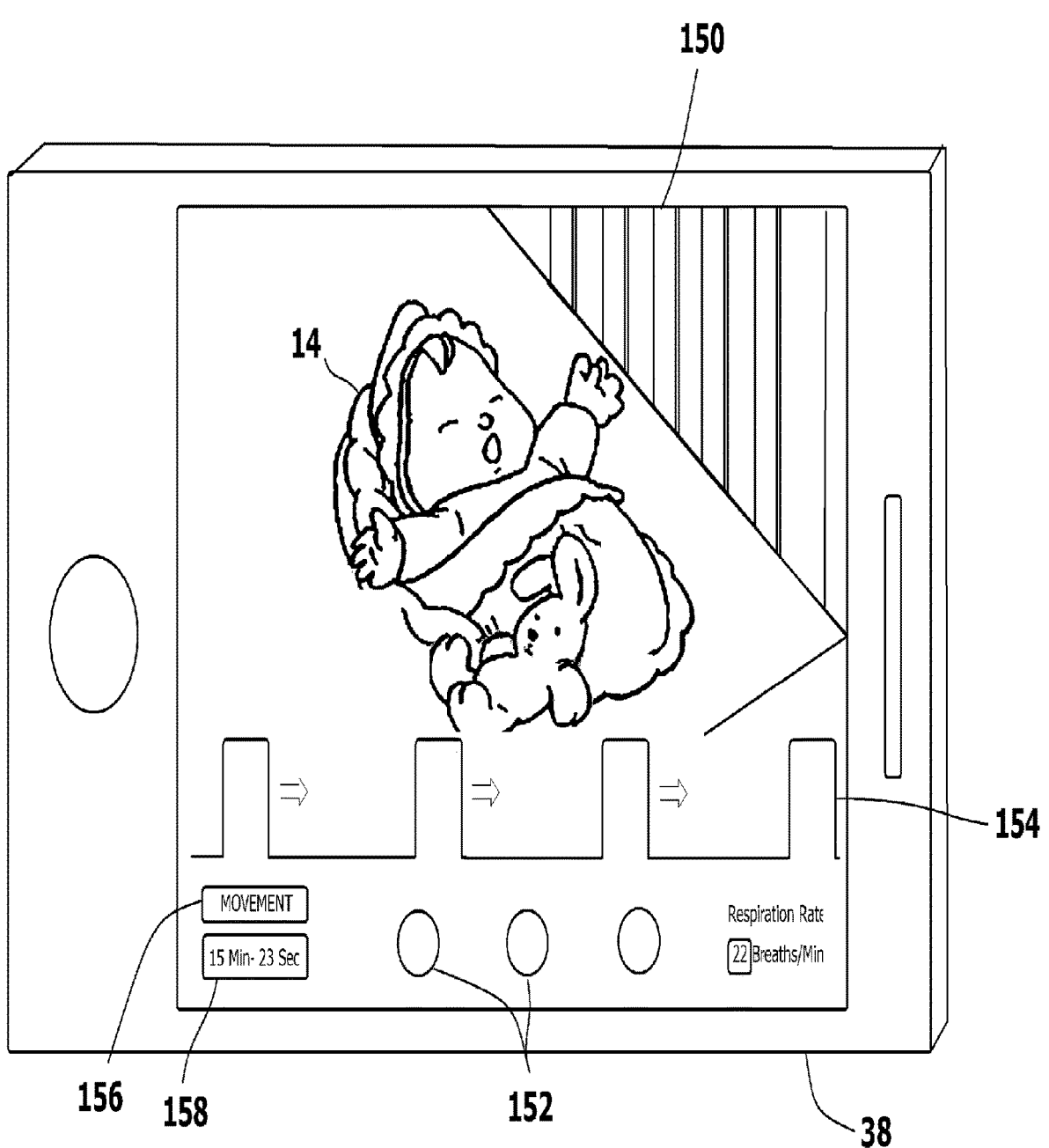
FIG. 9 shows an exemplary screen produced by a computing device that is used to interface with the monitoring unit of FIG. 2 and a user.

Referring to FIG. 9 in conjunction with FIG. 1 and FIG. 2, an exemplary screen 150 is shown that exemplifies what a user can see on his/her remote computing device 28. The screen 150 shows a live feed of the camera data 42. Also, on the screen 150 are various icons 152. By pressing the various icons 152, the observer 34 can elect to hear the audio feed from the monitoring unit 12, send an audio feed to the monitoring unit 12, and/or sound an alarm. Optional icons, such as autodialing of 911 and the like can also be included.

In addition to the live camera feed, the observer 34 can see a reproduction of a breathing waveform 154. The breathing waveform 154 can be the microphone derived breathing waveform 76, the camera derived breathing waveform 104, the radar derived breathing waveform 140, or a composite of any combination. The status 156 of the current state is shown, that is, the state of movement, breathing or no-breathing. The current state is also shown along with a time indication 158 that indicates the duration of that state. For example, in FIG. 9, the status 156 indicates a moving state and shows that the state has remained for the past 15 minutes. This may be an indication that the subject person 14 is awake.

Using the application software 30 of the remote computing device 28 and by menuing through the proper icons 152, the observer 34 can select to transmit his/her voice to the monitoring unit 12 in an attempt to quiet or assure the subject person 14. Alternatively, the observer 34 may elect to transmit music or a recorded story to the monitoring unit 12 to help the subject person 14 fall back to sleep.

It will be understood that the embodiment of the present invention that is illustrated and described is merely exemplary and that a person skilled in the art can make many variations to that embodiment. All such embodiments are intended to be included within the scope of the present invention as defined by the appended claims.

What is claimed is:

1. A method of monitoring a patient to detect life signs, comprising:
   providing a monitoring device to monitor a patient, wherein the monitoring device includes:
      a radar device to receive radar data corresponding to the patient,
      an image device to receive image data corresponding to the patient, and
      an audio device to receive audio data corresponding to the patient;
   receiving, during a first time period, at least one of:
      first radar data, with the radar device, indicative of movement,
      first image data, with the image device, indicative of movement, and
      first audio data, with the audio device, indicative of movement;
   determining, in the first time period, that at least one of the first radar data, the first image data, and the first audio data indicates movement comprising at least one first indication of movement and at least one second indication of movement;
   determining, in the first time period, that the at least one first indication of movement is from movement of the patient;
   determining, in the first time period, that the at least one second indication of movement is from a source other than movement of the patient;
   receiving, during a second time period:
      second radar data, with the radar device, indicative of a lack of movement of the patient,
      second image data, with the image device, indicative of the lack of movement of the patient, and
      second audio data, with the audio device, indicative of the lack of movement of the patient; and
   outputting a warning when:
      at least one of the first radar data, the first image data, and the first audio data indicates the movement of the patient during the first time period, and
      all of the second radar data, the second image data, and the second audio data indicates the lack of movement of the patient during the second time period.

2. The method of claim 1, wherein the outputting includes outputting the warning to a remote electronic device.

3. The method of claim 1, wherein the first image data includes at least one of visible light data or infrared light data.

4. The method of claim 1, wherein the monitoring device includes a light source, wherein the first image data is image data based on a reflection of light output by the light source.

5. The method of claim 1, wherein the monitoring device includes a radar source, wherein the first radar data is radar data based on a reflection of a radar wave output by the radar source.

6. The method of claim 5, wherein the radar source is a doppler radar source.

7. A method of monitoring a patient to detect life signs, comprising:

providing a monitoring device to monitor a patient, wherein the monitoring device includes:

a radar device to receive radar data corresponding to the patient, an image device to receive image data corresponding to the patient, and an audio device to receive audio data corresponding to the patient;

receiving, by the monitoring device, during a first time period, at least one of:

first radar data, with the radar device, indicative of movement, first image data, with the image device, indicative of movement, and first audio data, with the audio device, indicative of movement;

determining, by the monitoring device, that at least one of the first radar data, the first image data, and the first audio data indicates movement comprising first movement data with at least one first indication of movement and at least one second indication of movement;

that the at least one second indication of movement is from a source other than movement of the patient, and that the at least one first indication of movement is from movement of the patient;

outputting, by the monitoring device, based at least in part on the at least one first indication of movement, a first output indicating which of the first radar data, the first image data, and the first audio data indicates movement of the patient;

receiving, during a second time period, second movement data:

second radar data, with the radar device, indicative of a lack of movement of the patient, second image data, with the image device, indicative of the lack of movement of the patient, and second audio data, with the audio device, indicative of the lack of movement of the patient; and outputting, by the monitoring device, a warning based at least in part on the first movement data during the first time period and the second movement data during the second time period.

8. The method of claim 7, wherein the outputting the warning includes outputting the warning to a remote electronic device separate from the monitoring device.

9. The method of claim 7, wherein the first image data includes at least one of visible light data or infrared light data.

10. The method of claim 7, wherein the monitoring device includes a light source, wherein the first image data is image data based on a reflection of light output by the light source.

11. The method of claim 7, wherein the monitoring device includes a radar source, wherein the first radar data is radar data based on a reflection of a radar wave output by the radar source.

12. The method of claim 11, wherein the radar source is a doppler radar source.

13. The method of claim 11, further comprising:

receiving, by a remote electronic device separate from the monitoring device, the first output; and using, at least one screen of the remote electronic device, to show at least one reproduction of a plurality of waveforms, the plurality of waveforms comprising at least one first radar breathing waveform derived from the first radar data, at least one first image breathing waveform derived from the first image data, and at least one first audio breathing waveform derived from the first audio data, and wherein the at least one screen is configured to show whether one or more of the plurality of waveforms indicates movement of the patient.

14. The method of claim 13, further comprising using, the at least one screen of the remote electronic device, to show whether the first radar data, the first image data, and the first audio data indicates movement other than of the patient.

15. A method of monitoring a patient to detect life signs, comprising:

providing a monitoring device to monitor a patient, wherein the monitoring device includes:

a radar device to receive radar data corresponding to the patient, an image device to receive image data corresponding to the patient, and an audio device to receive audio data corresponding to the patient;

receiving, by the monitoring device, during a first time period, at least one of:

first radar data, with the radar device, indicative of movement, first image data, with the image device, indicative of movement, and first audio data, with the audio device, indicative of movement;

determining, by the monitoring device, that at least one of the first radar data, the first image data, and the first audio data comprises at least one first movement indication that indicates movement other than movement of the patient, and at least one of the first radar data, the first image data, and the first audio data comprises at least one second movement indication that indicates movement of the patient;

outputting, by the monitoring device, at least one of a first output indicating the at least one second movement indication that indicates movement of the patient, or a second output indicating the at least one first movement indication that indicates movement other than of the patient;

receiving, by a remote electronic device, at least one of the first output or the second output; and using, at least one screen of the remote electronic device, to show at least one of:

a first display element indicating whether the first radar data, the first image data, and the first audio data indicates movement of the patient, or a second display element indicating whether the first radar data, the first image data, and the first audio data indicates movement other than of the patient;

outputting, by the monitoring device or the remote electronic device, a warning when:

at least one of the first radar data, the first image data, and the first audio data indicates the movement of the patient during the first time period, and all of the second radar data, the second image data, and the second audio data indicates the lack of movement of the patient during the second time period.

16. The method of claim 15, wherein the first image data includes at least one of visible light data or infrared light data.

17. The method of claim 15, wherein the monitoring device includes a light source, wherein the first image data is image data based on a reflection of light output by the light source.

18. The method of claim 15, wherein the monitoring device includes a radar source, wherein the first radar data is radar data based on a reflection of a radar wave output by the radar source.

19. The method of claim 18, wherein the radar source is a doppler radar source.

20. The method of claim 18, wherein the using of the at least one screen includes showing, by the remote electronic device, both the first display element indicating whether the first radar data, the first image data, and the first audio data indicates movement of the patient, and the second display element indicating which of the first radar data, the first image data, and the first audio data indicates movement other than of the patient.

\* \* \* \* \*